United States Patent
Kashima et al.

(10) Patent No.: US 9,835,544 B2
(45) Date of Patent: Dec. 5, 2017

(54) BONDING STRENGTH TEST DEVICE FOR ELECTRONIC COMPONENTS AND METHOD FOR BONDING STRENGTH TEST

(71) Applicant: NHK SPRING CO., LTD., Yokohama-shi, Kanagawa (JP)

(72) Inventors: Hideki Kashima, Aiko-gun (JP); Yuji Sugita, Aiko-gun (JP); Takeshi Shimoda, Aiko-gun (JP); Tsutomu Fukuda, Aiko-gun (JP)

(73) Assignee: NHK SPRING CO., LTD., Tokyo (JP)

( * ) Notice: Subject to any disclaimer, the term of this patent is extended or adjusted under 35 U.S.C. 154(b) by 118 days.

(21) Appl. No.: 15/060,568

(22) Filed: Mar. 3, 2016

(65) Prior Publication Data

US 2016/0282257 A1    Sep. 29, 2016

(30) Foreign Application Priority Data

Mar. 25, 2015    (JP) .................. 2015-063062

(51) Int. Cl.
  *G01N 19/04* (2006.01)
  *G11B 5/455* (2006.01)
  *G11B 5/48* (2006.01)

(52) U.S. Cl.
  CPC ............. *G01N 19/04* (2013.01); *G11B 5/455* (2013.01); *G11B 5/483* (2015.09); *G11B 5/4853* (2013.01)

(58) Field of Classification Search
  None
  See application file for complete search history.

(56) References Cited

U.S. PATENT DOCUMENTS 4,567,758 A * 2/1986 Fisher ................... G01N 19/04
73/150 A

FOREIGN PATENT DOCUMENTS

| JP | 08111417 A | 4/1996 |
| JP | 11288986 A | 10/1999 |
| JP | 2002022650 A | 1/2002 |
| JP | 2009180620 A | 8/2009 |
| JP | 2012094237 A | 5/2012 |

* cited by examiner

*Primary Examiner* — Andre Allen
(74) *Attorney, Agent, or Firm* — Holtz, Holtz & Volek PC

(57) ABSTRACT

According to an embodiment, a bonding strength test device measures bonding strength between a flexure of a suspension of a hard disk drive and microactuators mounted on a gimbal of the flexure. The bonding strength test device includes a clamp, dummy, and device body. The clamp fixes the flexure. The dummy is adhered to the microactuators. The probe is engaged in the dummy. The device body measures a tensile load applied to the probe while the probe is pulled toward a direction to be apart from the flexure.

7 Claims, 12 Drawing Sheets

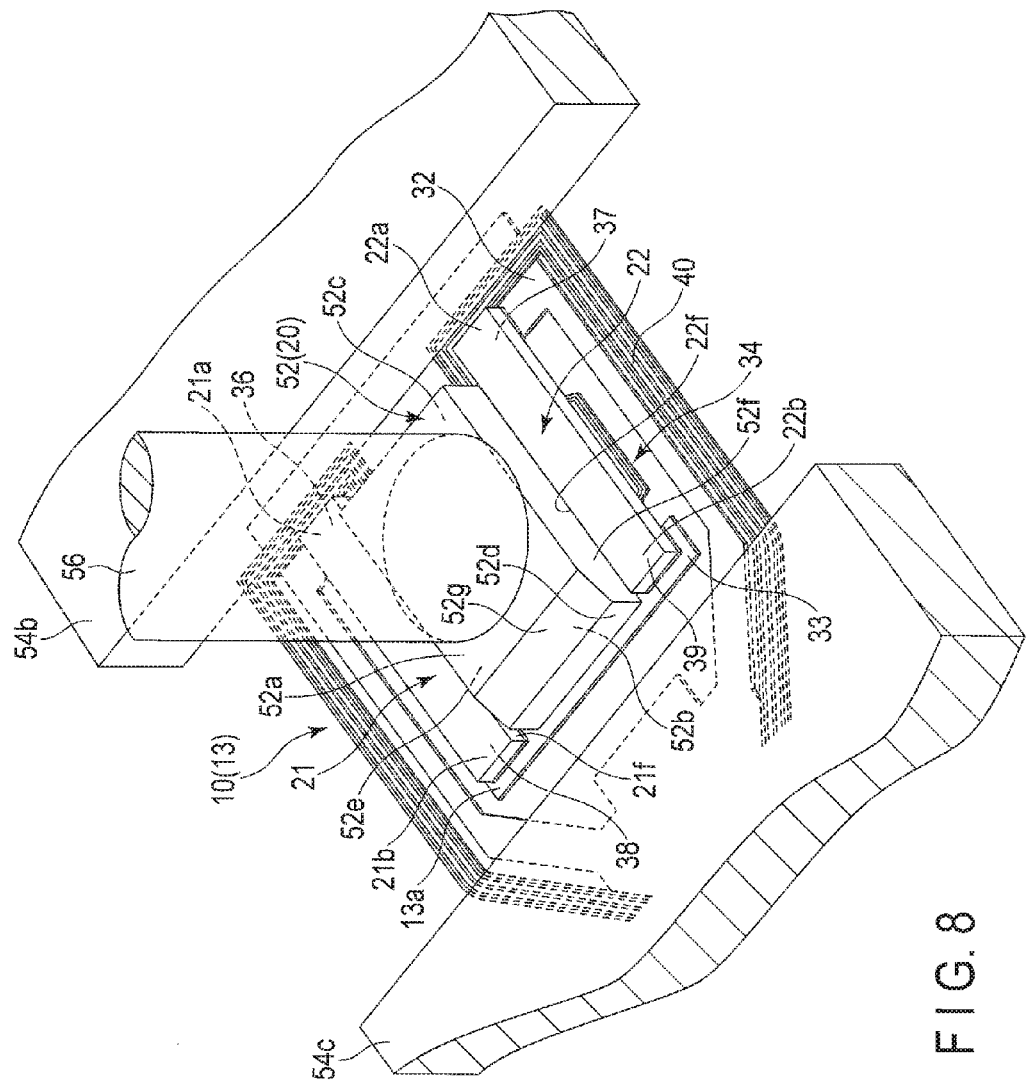
F I G. 8

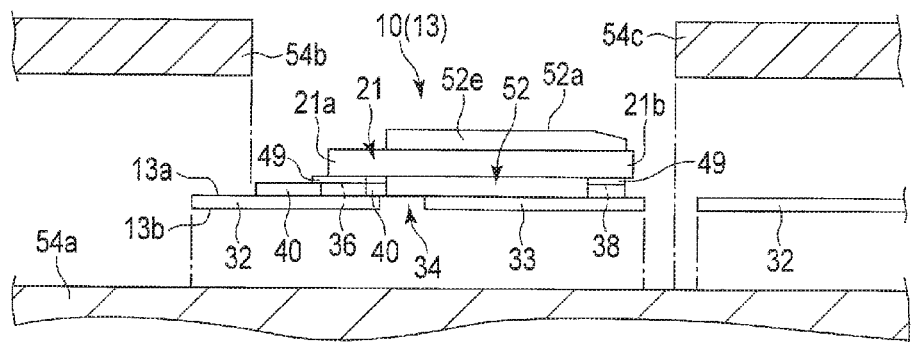
F I G. 10A
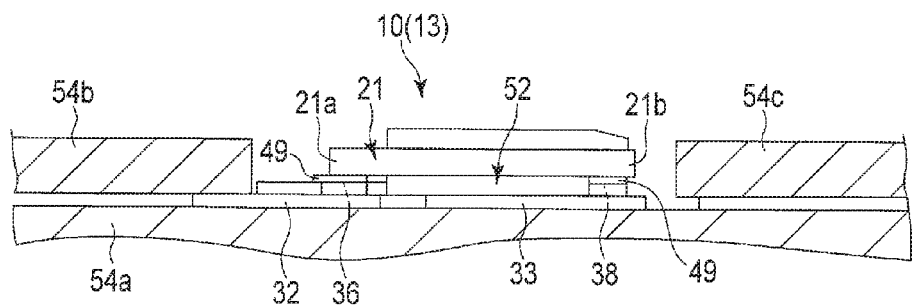
F I G. 10B
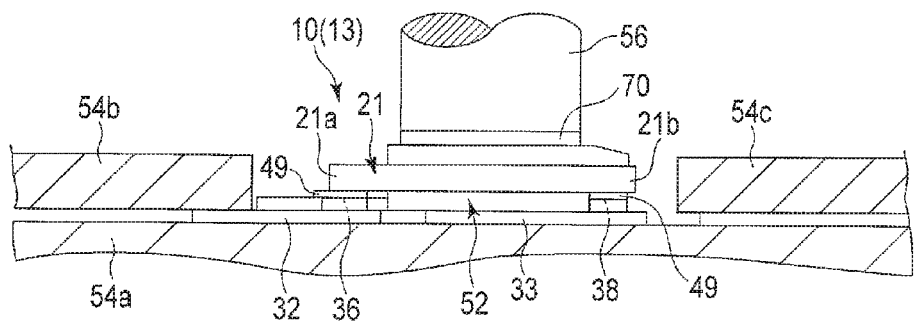
F I G. 10C
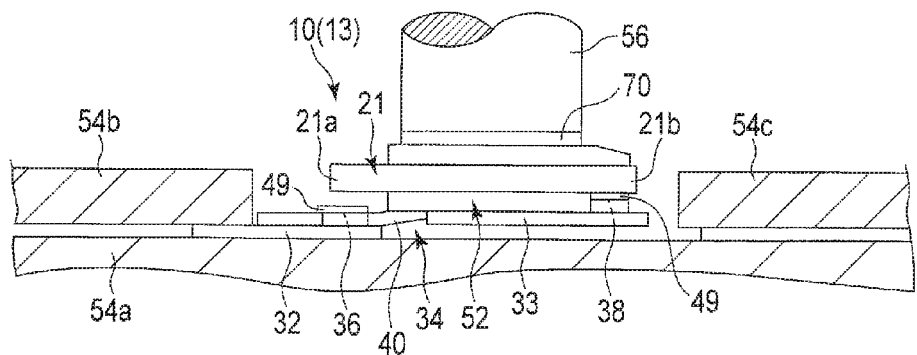
F I G. 10D

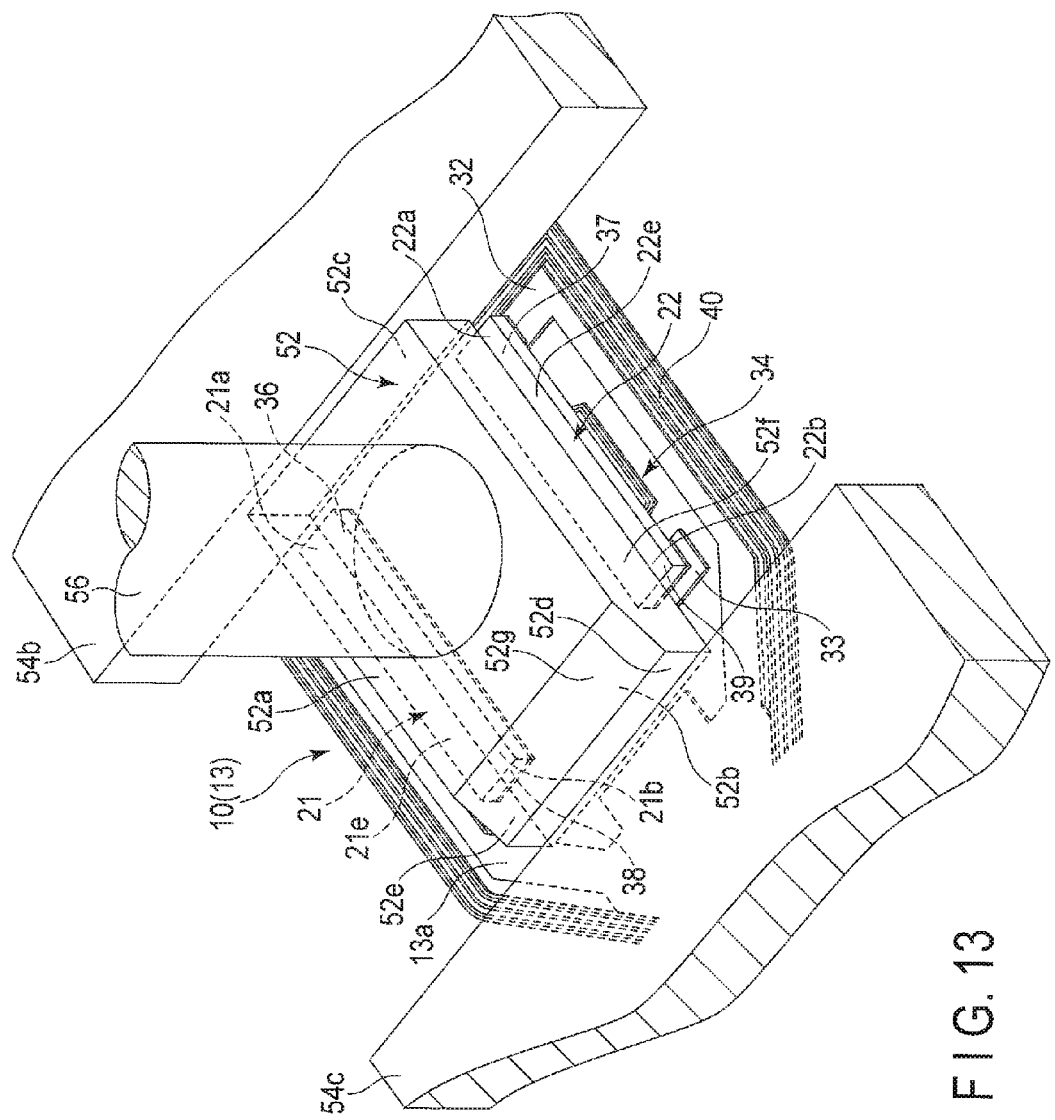
F I G. 13

BONDING STRENGTH TEST DEVICE FOR ELECTRONIC COMPONENTS AND METHOD FOR BONDING STRENGTH TEST

CROSS-REFERENCE TO RELATED APPLICATIONS

This application is based upon and claims the benefit of priority from prior Japanese Patent Application No. 2015-063062, filed Mar. 25, 2015, the entire contents of which are incorporated herein by reference.

BACKGROUND OF THE INVENTION

1. Field of the Invention

The present application relates generally to a bonding strength test device which measures bonding strength of an electronic component such as a microactuator mounted on the flexure of a hard disk drive, and a method for measuring bonding strength using the same device.

2. Description of the Related Art

To meet increasing recording density of hard disk drives, a microactuator including a piezoelectric device is often mounted on the suspension of the drive. The microactuator is an example of an electronic component.

As disclosed in JP 2012-94237 A (Patent Literature 1), a gimbal assembly in which a microactuator is mounted on a flexure at the tip of a suspension is known. In that case, such a microactuator must be miniaturized as compared to a case where a microactuator is mounted on the base plate of the suspension.

The contact surface of the microactuator and the flexure is reduced by the miniaturization, and the bonding strength therebetween becomes a quality control issue. As an evaluation method of bonding strength, a shear test is well-known as disclosed in JP 2002-22650 A (Patent Literature 2).

However, the bonding strength measured in a shear test is limited to sway directions. In addition to track width directions of the magnetic disk (sway directions), the flexure moves vertically in both the direction approaching the magnetic disk (loading direction) and the direction departing from the magnetic disk (unloading direction). Thus, impact of acceleration/deceleration is applied in the loading/unloading direction.

To improve the reliability of hard disk drives, a test method used for measuring bonding strength of microactuators in loading and unloading directions is demanded. There are, for example, proposed methods disclosed by JP 1996-111417 A (Patent Literature 3), JP 1999-288986 A (Patent Literature 4), and JP 2009-180620 A (Patent Literature 5) as means for measuring bonding strength of electronic components mounted on a substrate in their thickness direction.

However, with means disclosed by Patent Literatures 3 to 5, fixing of small and fragile microactuators to a test device is difficult to achieve.

Since a piezoelectric device which is a ceramic component of the microactuator lacks thermoplasticity, a fixing method by seizing disclosed in Patent Literature 3 cannot be adopted. Such a method is inappropriate for an additional reason that preparation for the test becomes complicated. Furthermore, since a piezoelectric device is weak, a fixing method by chucking disclosed in Patent Literature 4 is difficult to adopt. Furthermore, since a microactuator is small enough to be mounted on a flexure, a vacuum fixing method disclosed in Patent Literature 5 is difficult to adopt.

BRIEF SUMMARY OF THE INVENTION

The present application presents a bonding strength test device which measures bonding strength in loading and unloading directions of a small and fragile electronic component mounted on a flexure such as a microactuator, and a test method for measuring bonding strength using the same device.

According to an embodiment, a bonding strength test device measures bonding strength between a flexure of a suspension of a hard disk drive and an electronic component mounted on a gimbal of the flexure. The device includes a clamp to fix the flexure, a dummy to be adhered to the electronic component, a probe engaged in the dummy, and device body to measure a tensile load applied to the probe while the probe is pulled in a direction to be apart from the flexure.

According to this embodiment, the bonding strength in loading and unloading directions of the microactuator mounted on the flexure can be measured.

According to this embodiment, an adhesive agent may be added for engagement of the dummy and the probe. In this embodiment, if the electronic component is a pair of microactuators including a piezoelectric device formed of lead zirconate titanate, and the gimbal includes a first surface on which the pair of microactuators are arranged to be separated from each other and a second surface opposite to the first surface, the dummy may include side surfaces interposed between the microactuators while being adhered to inner side surfaces of the microactuator. The dummy may be a slider mounted on the gimbal. Or, the dummy may be disposed on both upper surfaces of the pair of microactuators to be adhered thereto. At that time, the dummy may be a slider having an outer dimension larger than that of a slider mounted on the flexure.

Furthermore, according to an embodiment, a method for measuring bonding strength between a flexure of a suspension of a hard disk drive and an electronic component of a gimbal of the flexure is presented. In this method, the electronic component is a microactuator including a piezoelectric device formed of lead zirconate titanate, the flexure is fixed to a clamp, a dummy is adhered to the microactuator, a probe is engaged in the dummy, and the tensile load between the probe and the flexure is measured while the probe is pulled in a direction to be apart from the flexure.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 8 is a perspective view in which a dummy and a flexure of FIG. 7 are shown in an enlarged manner.

FIG. 10A is a schematic view which shows a subsequent step to FIG. 9D.

FIG. 10B is a schematic view which shows a subsequent step to FIG. 10A.

FIG. 10C is a schematic view which shows a subsequent step to FIG. 10B.

FIG. 10D is a schematic view which shows a subsequent step to FIG. 10B.

FIG. 13 is a perspective view of a dummy of a bonding strength test device of a second embodiment.

DETAILED DESCRIPTION OF THE INVENTION

First, an example of a flexure of a suspension of a hard disk drive which is a target of evaluation of a bonding strength test of the present application will be explained with reference to FIGS. 1 to 6.

Figure 1:
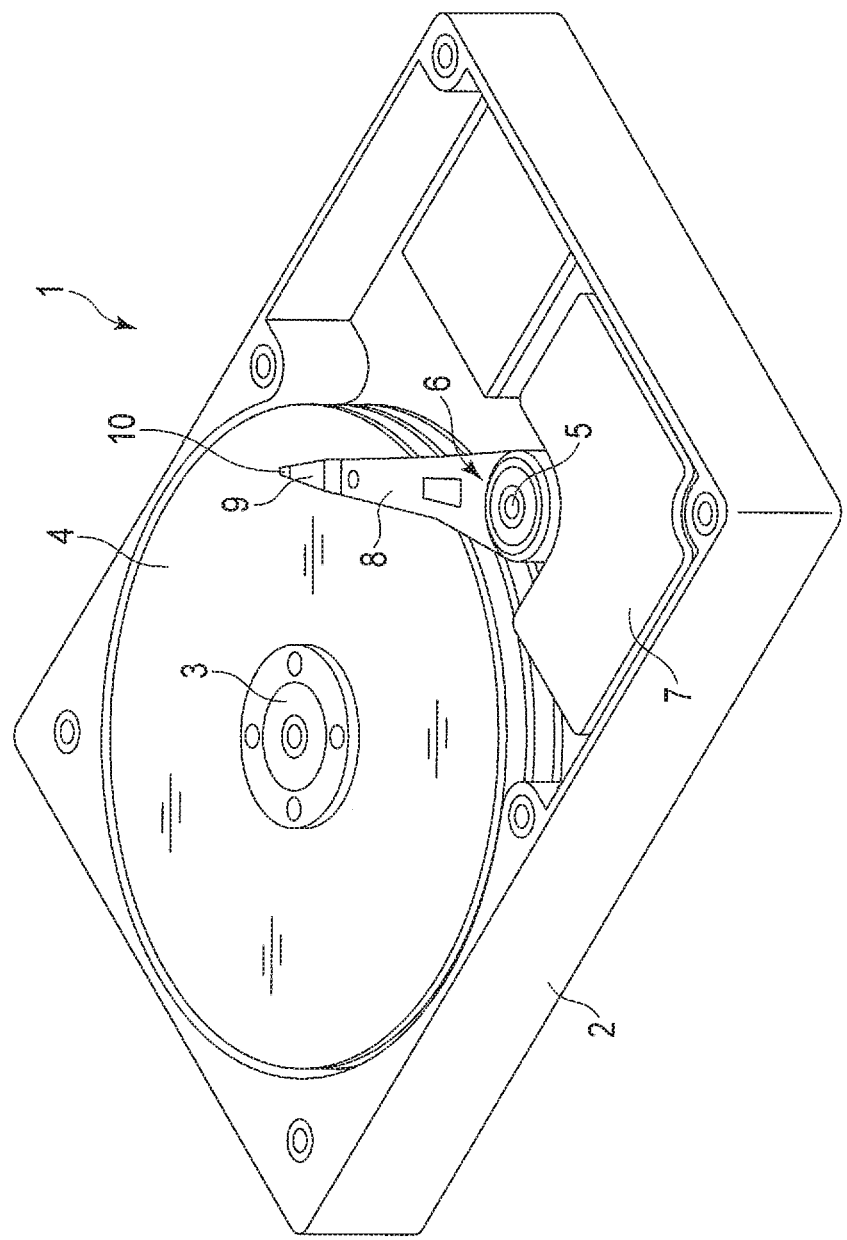
FIG. 1 is a perspective view which shows an example of a hard disk drive.

FIG. 1 shows a hard disk drive (HDD) 1 including, for example, a case 2, disk 4 rotated around a spindle 3, a carriage 6 pivoted on a pivot axis 5, and voice coil motor (primary actuator) 7 for driving the carriage 6. The case 2 is sealed by a lid which is not shown.

An arm 8 is provided with the carriage 6. A suspension 9 is attached to the tip of the arm 8. A slider 20 is arranged on the tip of the suspension 9 as a component of a magnetic head (as in FIG. 3). When the disk 4 rotates at high speed, air is introduced between the disk 4 and a floating surface 20a of the slider 20 and an air bearing is produced therebetween.

When the carriage 6 is rotated by the voice coil motor 7, the suspension 9 moves within the radius of the disk 4 such that the slider 20 can reach a desired track of the disk 4.

Figure 2:
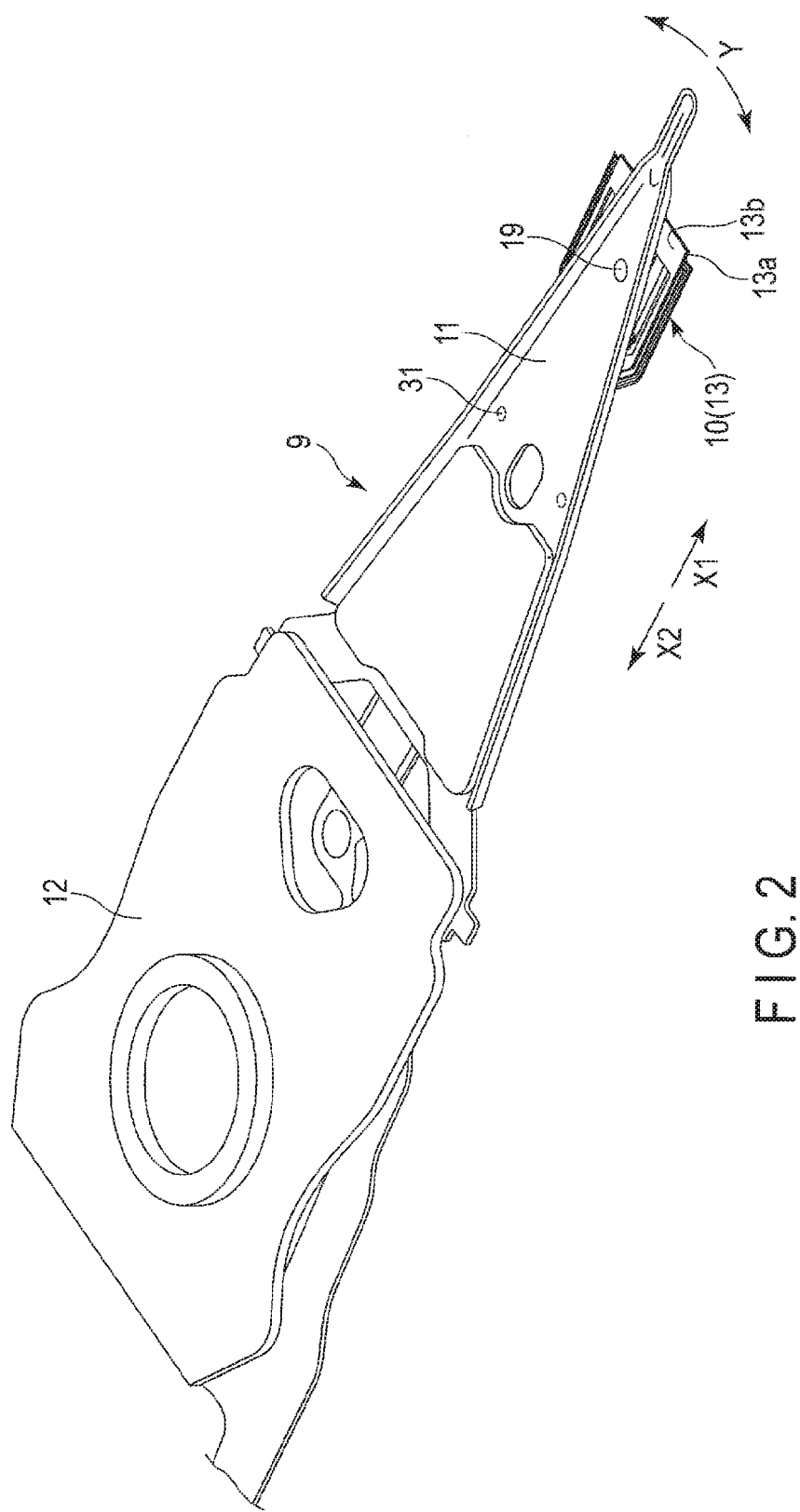
FIG. 2 is a perspective view which shows a suspension of FIG. 1.

The suspension 9 of FIG. 2 includes, for example, a base plate 12 fixed to the arm 8 of the carriage 6 (as in FIG. 1), load beam 11, and conductor-provided flexure 10.

Arrows X1 and X2 of FIG. 2 show longitudinal directions of the suspension 9, that is, the flexure 10 where X1 points to its distal end and X2 points to its proximal end. Arrow Y of FIG. 2 shows sway directions (the width direction of the slider 20). The flexure 10 is arranged along the load beam 11, and a gimbal 13 and the like are provided with the tip of the flexure 10. The gimbal 13 includes a second surface 13b which is opposed to the load beam 11 and a first surface 13a which is opposite to the second surface 13b and on which the slider 20 is mounted.

Figure 3:
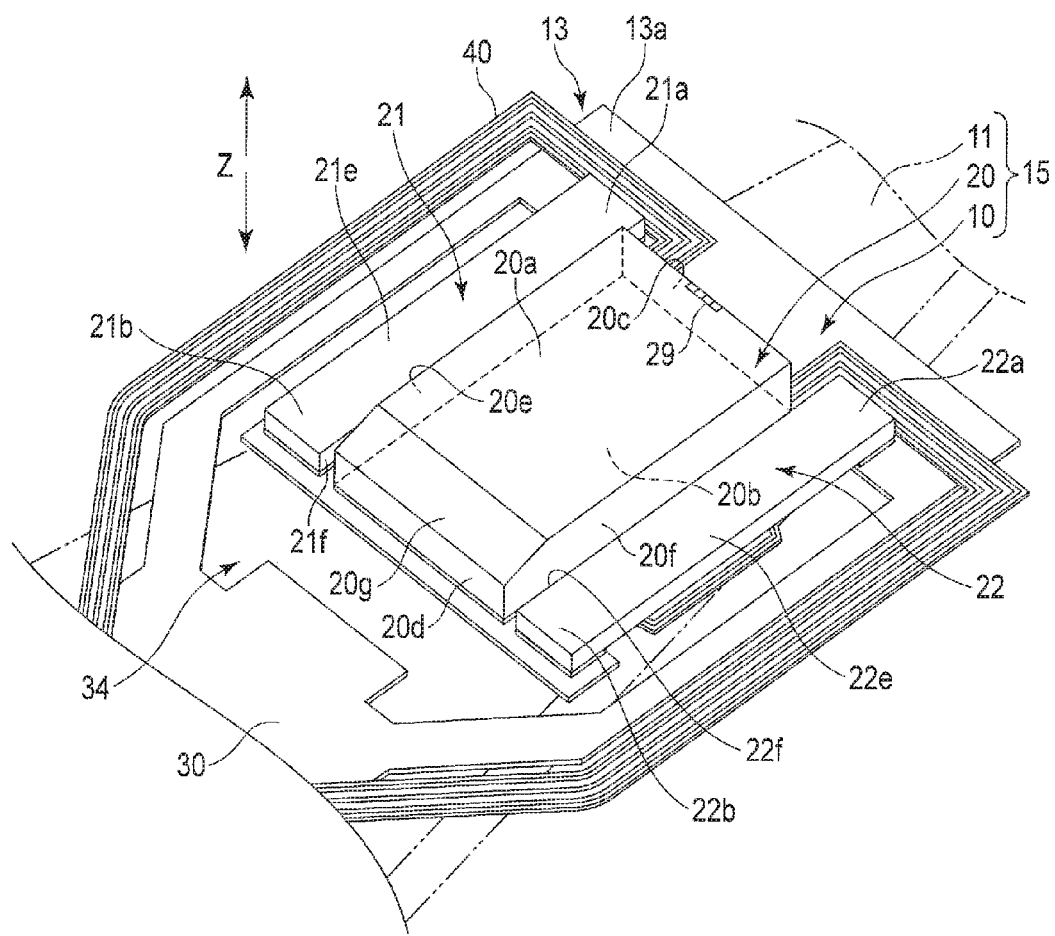
FIG. 3 is a perspective view which shows a flexure of FIG. 2.

FIG. 3 is a perspective view which shows the gimbal 13 as being viewed from the first surface 13a side. The slider 20 is formed of a ceramic with excellent density such as $Al_2O_3$—TiC (ALTIC) in the shape of a substantially flat plate. The slider 20 includes the floating surface 20a opposed to the disk 4, fixing surface 20b which is opposite to the floating surface 20a, and four side surfaces 20c, 20d, 20e, and 20f connecting the floating surface 20a and the fixing surface 20b.

The floating surface 20a of the slider 20 is at least partly polished very smoothly. The end of the slider 20 (for example, side surface 20d facing the proximal end of the flexure 10) has an inclined surface 20g formed continuing to the floating surface 20a. By the rotation of the disk 4, air is introduced between the slider 20 and the disk 4 via the inclined surface 20g. Hereinafter, in the present application, the air inlet side may be referred to a leading side and the air outlet side may be referred to as trailing side with respect to the slider 20 and the gimbal 13.

A magnetoresistive (MR) device 29 is provided with an end of the slider 20 (side surface 20c in the trailing side, for example) of the magnetic head, the MR device 29 configured to convert magnetic signals into electrical signals, for example. The MR device 29 accesses the disk 4 to write and read. Arrow Z of FIG. 3 shows loading and unloading directions of the magnetic head (the thickness direction of the slider 20). The slider 20, load beam 11, and flexure 10 are main components of a head gimbal assembly 15.

A pair of microactuators (secondary actuators) 21 and 22 are mounted on the first surface 13a of the gimbal 13 of the flexure 10. The microactuators 21 and 22 are arranged on the sides of the slider 20, respectively, to deflect the slider 20 in sway directions. The microactuators 21 and 22 are an example of electronic components (microdevices) to be mounted on the head gimbal assembly 15. The head gimbal assembly 15 may include an additional electronic component such as a laser diode used for laser-assisted recording.

The microactuators 21 and 22 are formed in a plate-like shape along the side surfaces 20e and 20f of the slider 20 keeping a slight distance therefrom. The microactuators 21 and 22 include, respectively, first ends 21a and 22a in the trailing side and second ends 21b and 22b in the leading side. Furthermore, the microactuators 21 and 22 include, respectively, inner side surfaces 21f and 22f which are opposed to the side surfaces 20e and 20f of the slider 20, and upper surfaces 21e and 22e which are in the opposite side of the gimbal 13.

Figure 4:
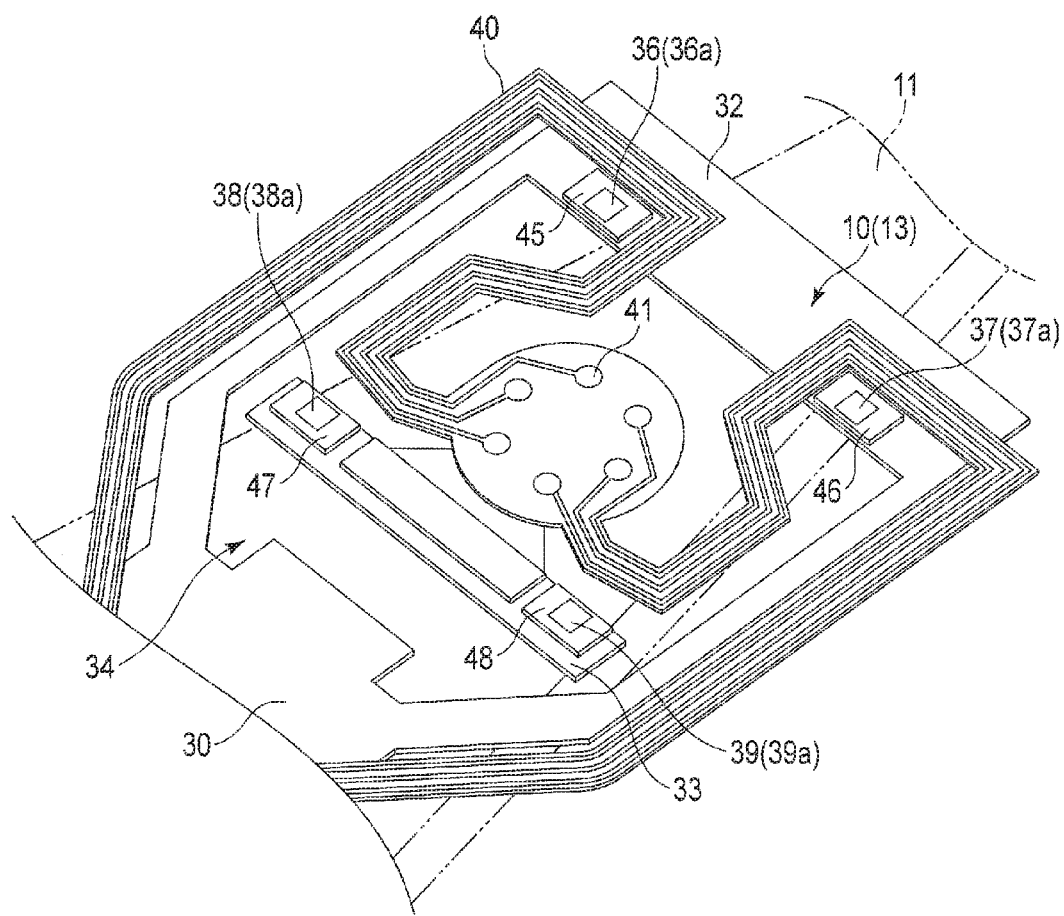
FIG. 4 is a perspective view which shows the flexure of FIG. 3 omitting a slider and microactuators from the depiction.

FIG. 4 is a perspective view which shows the gimbal 13 of FIG. 3 omitting the slider 20 and microactuators 21 and 22. The flexure 10 includes a metal base 30 of a stainless steel plate and an interconnection 40 arranged along the metal base 30.

The metal base 30 is fixed to the load beam 11 by a plurality of welds 31 (shown in FIG. 2) formed through, for example, a laser welding process. The metal base 30 includes an outrigger 32 and a tongue 33 on the gimbal 13. The outrigger 32 is formed continuing to the welds 31 and includes an opening 34. The tongue 33 is formed separately from the outrigger 32 and is disposed inside the opening 34 of the outrigger 32.

Figure 5:
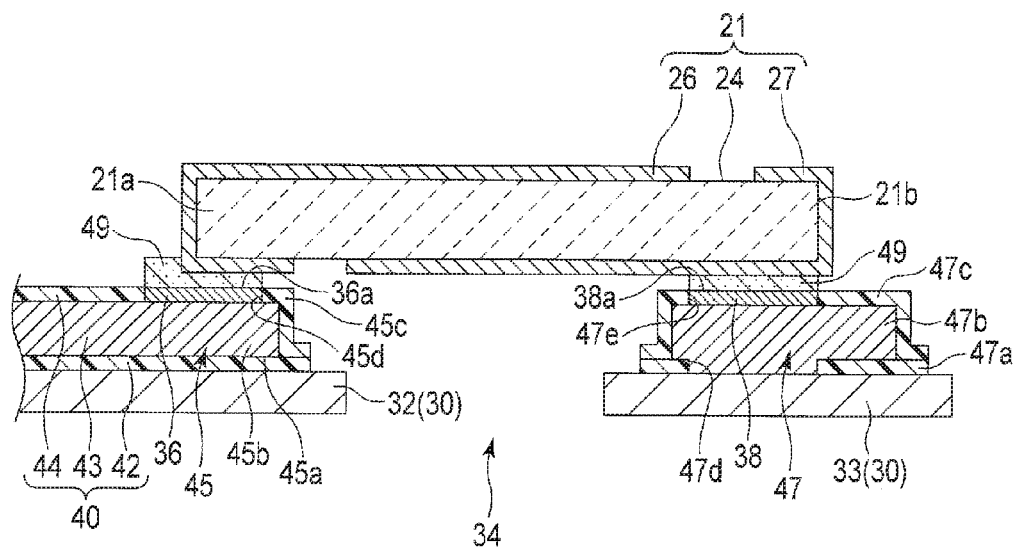
FIG. 5 is a schematic view which shows a cross-section of a connection part of a microactuator of FIG. 3.

The interconnection 40 partly overlaps the metal base 30 and partly does not. Since the interconnection 40 is flexible, it is deformable at the part which does not overlap the metal base 30. One end of the interconnection 40 is electrically connected to a plurality of electrodes 41 arranged in the tongue 33. The other end of the interconnection 40 is extended toward the base plate 12 (the distal end side of the suspension 9). The interconnection 40 includes an insulating layer 42 which is formed of an insulating material such as polyimide and is formed on the metal base 30. The interconnection 40 further includes, for example, a conductor pattern 43 formed on the insulating layer 42, and a cover layer 44 which is formed of an insulating material such as polyimide and covers the conductor pattern 43. They are depicted in FIG. 5. The conductor pattern 43 is electrically connected to the MR device 29 of the slider 20 (which is shown in FIG. 3) through the electrodes 41.

The tongue 33 is hung by the flexible interconnection 40 while being separated from the outrigger 32. That is, the tongue 33 and the outrigger 32 are connected to each other in such a manner that they can swing. A dimple 19 (shown in FIG. 2) is formed in the proximity of the tip of the load beam 11 to project toward the tongue 33. The gimbal 13 is structured to allow a swing with respect to the load beam 11 around a connecting point of the dimple 19 and the tongue 33.

The flexure 10 further includes a pair of first pads 45 and 46 provided in the tip side of the outrigger 32 and a pair of second pads 47 and 48 provided with the tongue 33. On the first pads 45 and 46, first fitting pads 36 and 37 are formed. On the second pads 47 and 48, second fitting pads 38 and 39 are formed.

FIG. 5 is a cross-sectional view which shows how first and second ends 21a and 21b of the microactuator 21 are mechanically fixed to and electrically connected to the flexure. Between the pair of the microactuators 21 and 22, only microactuator 21 is exemplified hereinafter since the other microactuator 22 includes similarly structured first and second ends 22a and 22b.

The microactuator 21 includes a piezoelectric device 24 which is formed of a piezoelectric material such as lead zirconate titanate (PZT). The microactuator 21 further includes a first electrode 26 which is formed around the piezoelectric device 24, and a second electrode 27. The first electrode 26 is formed at one end surface of the piezoelectric device 24 to go along its upper surface. The second electrode 27 is formed at the other end surface of the piezoelectric device 24 to go along its lower surface. The piezoelectric device 24 has, for example, a length of 1.5 mm (0.5 to 2.5 mm), a width of 0.25 mm (0.15 to 0.50 mm), and a thickness of 0.09 mm (0.05 to 0.20 mm).

The first end 21a of the microactuator 21 is fixed to an upper surface 36a of the first fitting pad 36 on the outrigger 32 by a conductive adhesive agent (for example, silver paste) 49. The second end 21b of microactuator 21 is fixed to an upper surface 38a of the second fitting pad 38 on the tongue 36 by the conductive adhesive agent 49. The height between the metal base 30 and the upper surface 36a of the first fitting pad 36 and the height between the metal base 30 and the upper surface 38a of the second fitting pad 38 are the same. Note that, hereinafter in the present application, the upper surfaces 36a, 37a, 38a, and 39a of the first and second fitting pads 36, 37, 38, and 39 may be referred to as contact surfaces.

The contact surfaces (upper surfaces) 36a and 38a of the first and second fitting pads 36 and 38 to which the first and second electrodes 26 and 27 are attached are each formed in a square such as 0.11 (0.08 to 0.80) mm². Note that the first and second fitting pads 36 and 38 may each be formed to be circular in that case, the contact surfaces 36a and 38a in circles may each be formed to have a diameter of 0.12 (0.08 to 0.80) mm.

The first pad 45 includes, for example, an insulating layer 45a formed, continuing to the insulating layer 42 of the interconnection 40, conductor pattern 45b formed continuing to the conductor pattern 43, and cover layer 45c formed continuing to the cover layer 44. The cover layer 45c includes an opening 45d. The first fitting pad 36 is formed in an opening 45d of the first pad 45 and is electrically connected to the conductor pattern 43 of the interconnection 40 through the conductor pattern 45b.

The second pad 47 includes, for example, an insulating layer 47a formed on the metal base 30, conductor pattern 47b formed on the insulating layer 47a, and cover layer 47c covering the conductor pattern 47b. The insulating layer 47a and the cover layer 47c include openings 47d and 47e. The second fitting pad 38 is formed in the opening 47e of the second pad 47 and is electrically connected to the metal base 30 (tongue 33) through the conductor pattern 47b.

The first electrode 26 of microactuator 21 is electrically connected to the conductor pattern 43 of the interconnection 40 through the conductive adhesive agent 49 on the first fitting pad 36. The second electrode 27 is electrically connected to the metal base 30 which is a conductor in the ground side through the conductive adhesive agent 49 on the second fitting pad 38.

Figure 6:
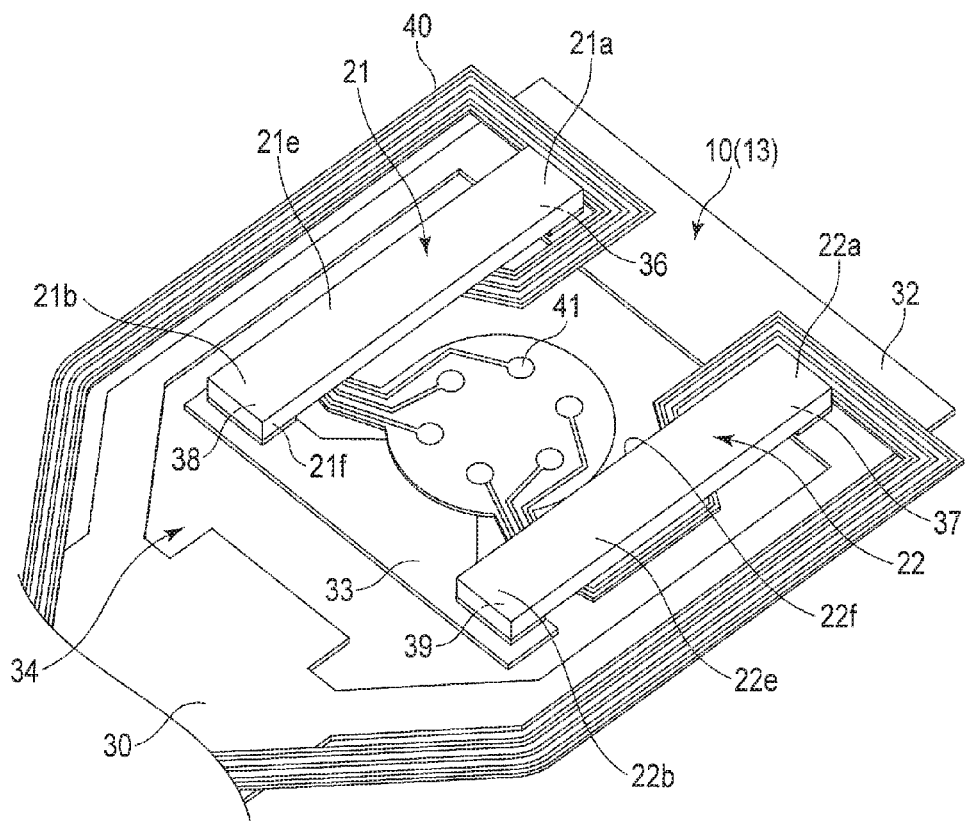
FIG. 6 is a perspective view of the flexure which is a target of a bonding strength test of the present application.

FIG. 6 shows an example of the flexure of the suspension of the hard disk drive, which is a target of the bonding strength test of the present application. In the test, the flexure 10 which is not fixed to the load beam 11 is evaluated. Furthermore, as depicted, the slider 20 is not attached or soldered to the flexure 10. To the contrary, the slider 20 of FIG. 3 has the leading side of the fixing surface 20b which is fixed in between the second fitting pads 38 and 39 by an insulating adhesive agent and the center of the fixing surface 20b which is soldered to a plurality of electrodes 41.

Figure 7:
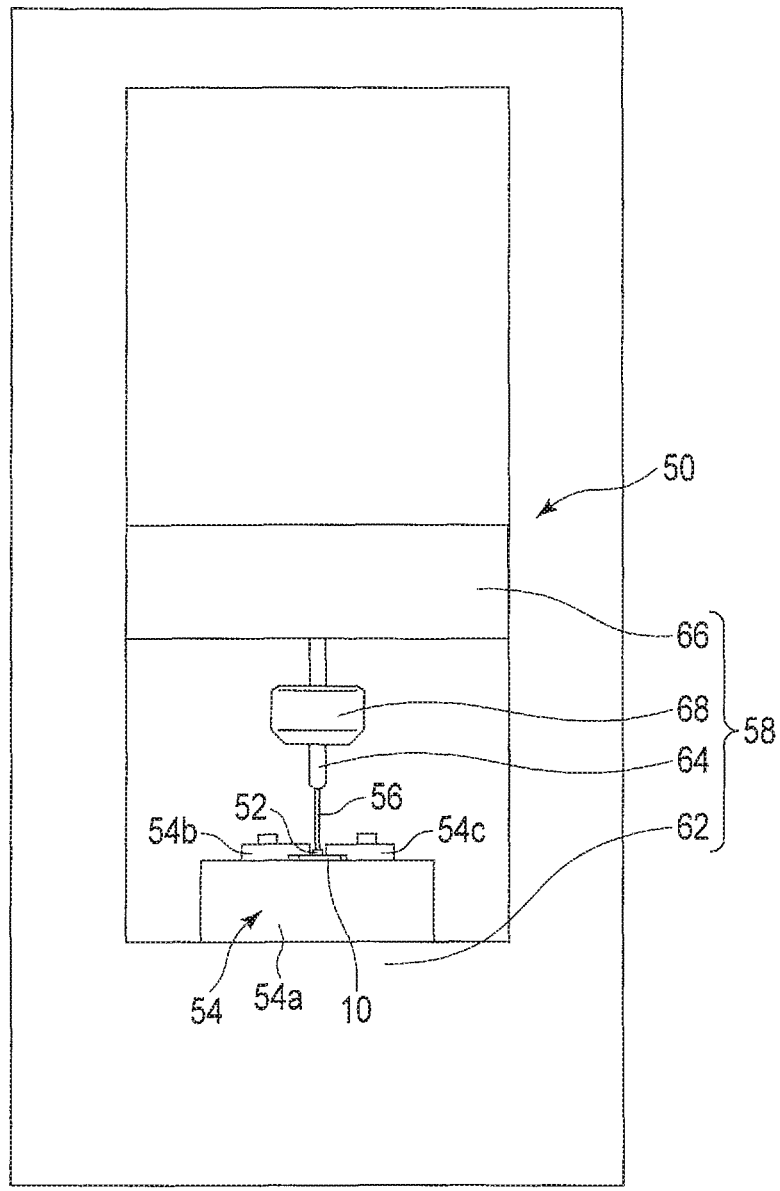
FIG. 7 shows the entirety of the bonding strength test device of the first embodiment of the present application.

Now, an example of a bonding strength test device 50 of a first embodiment of the present application will be explained with reference to FIGS. 7 and 8. The bonding strength test device 50 includes a dummy 52, clamp 54, probe 56, and device body 58.

In the present embodiment, the dummy 52 is the slider 20 (as in FIG. 3) which is manufactured to be mounted on the gimbal 13 of the hard disk drive 1. The dummy 52 includes a floating surface 52a, fixing surface 52b, and side surfaces 52c, 52d, 52e, and 52f, and inclined surface 52g which corresponding to the floating surface 20a, fixing surface 20b, side surfaces 20c, 20d, 20e, and 20f, and inclined surface 20g of the slider 20, respectively.

The dummy 52 is mounted on the gimbal 13 of the flexure 10, and the side surfaces 20e and 20f are adjacent to the microactuators 21 and 22, respectively. The side surfaces 20e and 20f of the dummy 52 may be referred to as adjacent surfaces which are adjacent to the microactuators 21 and 22. The side surfaces 20e and 20f are adhered to the inner side surfaces 21f and 22f of the microactuators 21 and 22 by an adhesive agent 70 (as in FIG. 9D).

The clamp 54 is provided with the lower part of the device body 58 to detachably attach the flexure 10 to the device body 58. The clamp 54 includes a base member 54a fixed to the device body 58, first and second holding plates 54b and 54c which hold the trailing side and the leading side of the outrigger 32 of the metal base 30 with the base member 54a, and a plurality of bolts to fasten the first and second holding plates 54b and 54c to the base member 54a.

Note that the clamp 54 of the present embodiment includes riot only a clamp provided with the device body 58 by which the flexure 10 is directly fixed to the device body 58 but also a vise to which the flexure 10 is fixed to be mounted on the device body 58. When the flexure is fixed by the vise, the vise should have a weight which requires a force greater than the contact force of the microactuators 21 and 22 to be hung.

The probe 56 is formed in a rod-like shape extending vertically and is hung from the device body 58. The lower end of the probe 56 is opposed to the gimbal 13 of the flexure 10 which is fixed to the clamp 54 and is engaged in the floating surface 52a of the dummy 52 by the adhesive agent 70 (shown in FIG. 10C).

That is, the probe 56 and microactuators 21 and 22 are engaged together by means of the dummy 52. The dummy 52 may be referred to as, for example, an intermediate member, adjacent member, solid member, or block.

The device body 58 is a conventional pull-test device which includes, for example, a table 62 on which the clamp 54 is disposed, chuck 64 which detachably attaches the proximal end of the probe 56, mobile unit 66 which moves the chuck 64 or the table 62 up and down, and measurement unit (load cell) 68 which measures load applied to the probe 56. In the example of FIG. 7, the chuck 64 is on the movable side and the table 62 is on the fixing side.

Now, steps of a bonding strength test method in which the bonding strength test device 50 of the present embodiment is used will be explained with reference to FIGS. 9A to 10D. FIGS. 9A to 9D are schematic views of the gimbal 13 of the flexure 10 as being viewed from the trailing side. FIGS. 10A to 10D are schematic views of the gimbal 13 as being viewed from the side in which microactuator 21 is mounted.

Figure 9A:
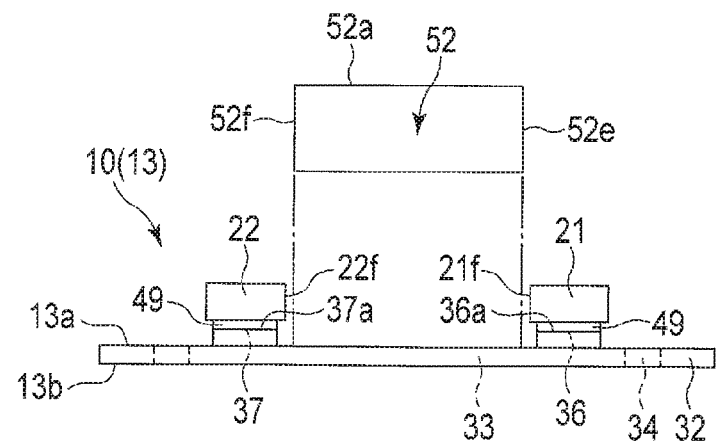
FIG. 9A is a schematic view which shows a step of the bonding strength test method in which the bonding strength test device of the first embodiment is used.
Figure 9B:
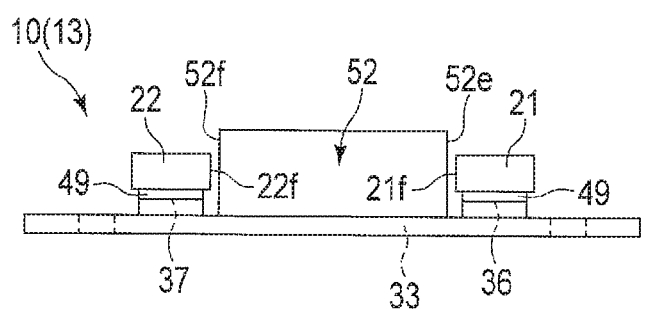
FIG. 9B is a schematic view which shows a subsequent step to FIG. 9A.

First, the dummy 52 having the same shape and formed of the same material as the slider 20 is mounted on the gimbal 13 of the flexure 10 of FIG. 6 (cf. FIG. 9A). In this state, the dummy 52 is not fixed to the tongue 33 of the metal base 30 and is not mechanically connected to the tongue 33 (cf. FIG. 9B).

Figure 9C:
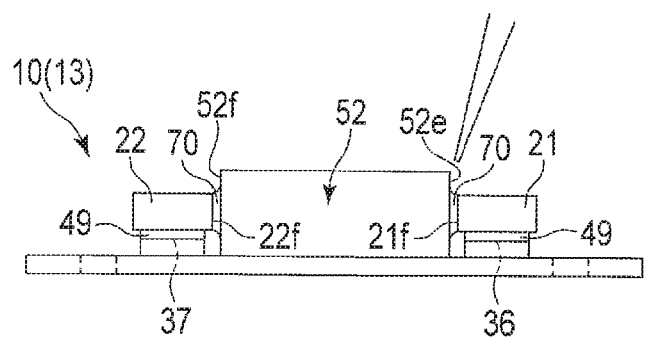
FIG. 9C is a schematic view which shows a subsequent step to FIG. 9B.
Figure 9D:
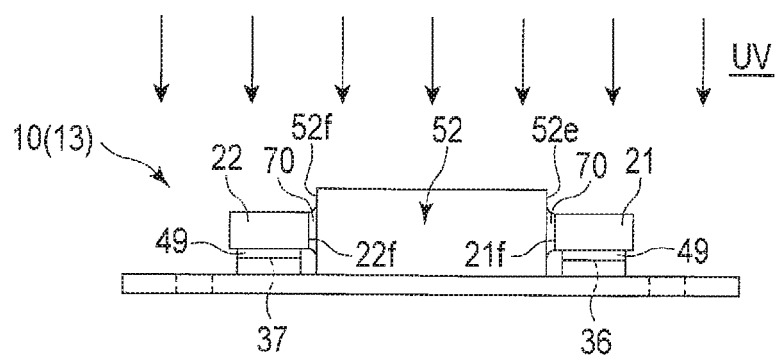
FIG. 9D is a schematic view which shows a subsequent step to FIG. 9C.
Figure 11A:
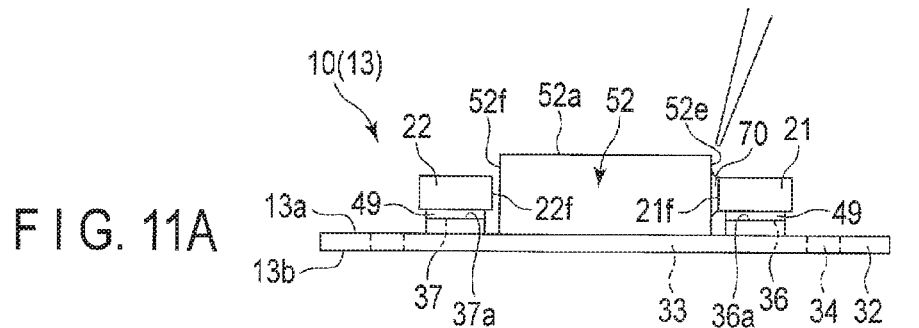
FIG. 11A is a schematic view which shows a first variation of the bonding strength test method explained with reference to FIGS. 9A to 10D.
Figure 11B:
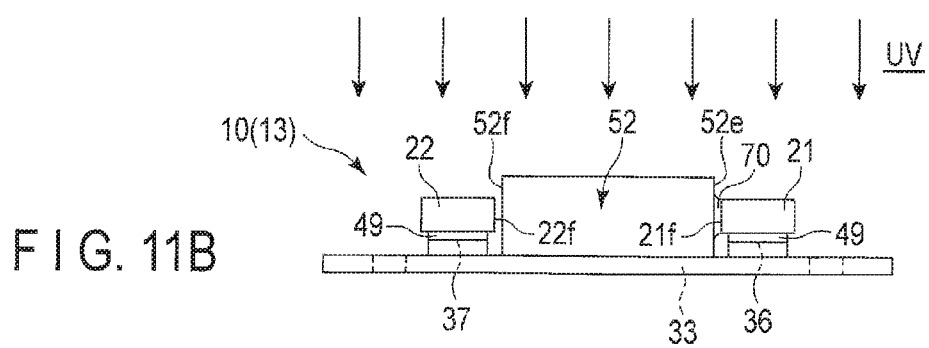
FIG. 11B is a schematic view which shows a subsequent step to FIG. 11A.
Figure 11C:
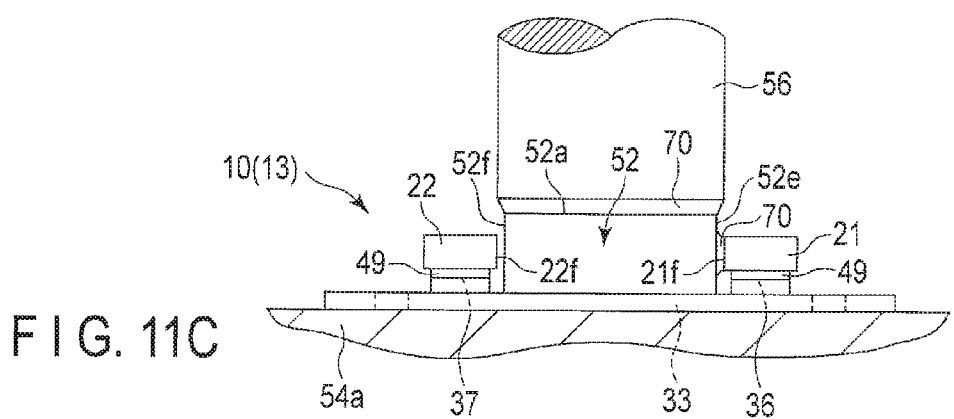
FIG. 11C is a schematic view which shows a subsequent step to FIG. 11B.
Figure 11D:
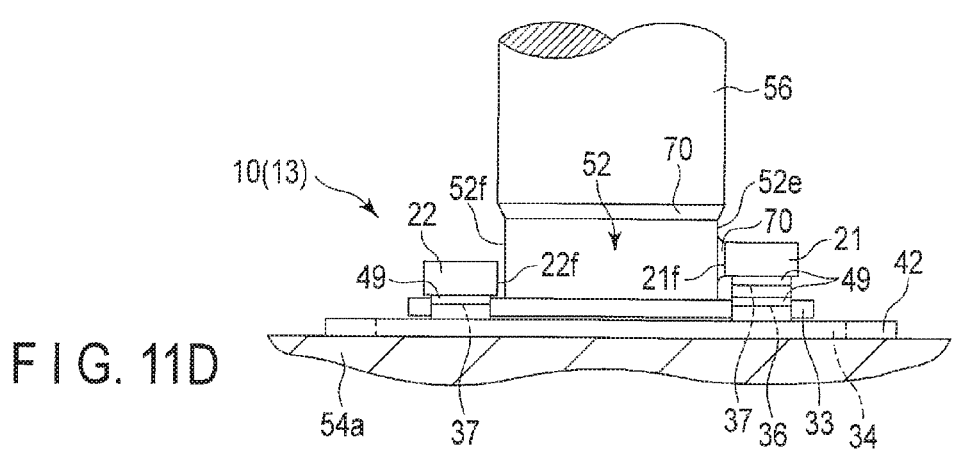
FIG. 11D is a schematic view which shows a subsequent step to FIG. 11C.

An ultraviolet-cured adhesive agent 70 is injected between the inner side surfaces 21f and 22f of microactuators 21 and 22 and the dummy 52 (cf. FIG. 9C). The adhesive agent 70 is cured by ultraviolet irradiation to adhere the inner side surfaces 21f and 22f to the dummy 52 (cf. FIG. 9D). The adhesive agent 70 may be used more to adhere the tongue 33 of the metal base 30 to the dummy 52 in addition to the microactuators 21 and 22.

The flexure 10 in which the dummy 52 is adhered to microactuators 21 and 22 is mounted on the base member 54a of the clamp 54 (cf. FIG. 10A). The outrigger 32 of the metal base 30 is fixed by the first and second holding plates 54b and 54c of the clamp 54 (cf. FIG. 10B). In this state, the tongue 33 of the metal base 30 is not fixed to the first and second holding plates 54b or 54c, and the tongue 33 overlaps the outrigger 32 by the interconnection 40 and microactuators 21 and 22.

The chuck 64 is lowered such that the lower end of the probe 56 approaches the dummy 52. The ultraviolet-cured adhesive agent 70 is injected between the lower end of the probe 56 and the dummy 52, and then ultraviolet is irradiated thereon. The lower end of the probe 56 and the dummy 52 are engaged (adhered) by the cured adhesive agent 70 (cf. FIG. 10C).

The chuck 64 is then raised at a constant speed to measure a tensile load applied to the probe 56. The dummy 52 is pulled in a direction to be apart from the flexure 10 by the probe 56. The first ends 21a and 22a of the microactuators 21 and 22 are peeled off one after another from the contact surfaces 36a and 37a of the first fitting pads 36 and 37 (cf. FIG. 10D). The bonding strength test method explained with reference to FIGS. 9A to 10D is an example of the bonding strength test method of the present application.

The bonding strength test device 50 as above can accurately measure the load of the magnetic head and bonding strength (peel strength) in the unloading direction with respect to the electronic component mounted on the gimbal 13 of the flexure 10. Therefore, the bonding strength of the microactuators 21 and 22 and the first fitting pads 36 and 37 can be evaluated accurately. As a result, the bonding strength of the flexure 10 is qualified. Furthermore, the lower surface of the dummy 52 (fixing surface 52b) is supported by the first surface 13a of the gimbal 13. Thus, if the probe 56 and the dummy 52 erroneously contact each other while the probe 56 is made closer to the dummy 52, the stress by the probe 56 is not easily transferred to the microactuators 21 and 22. Therefore, the flexure 10 can accurately be evaluated without causing damage to the contact surfaces 36a and 37a of the first fitting pads 36 and 37.

Furthermore, in the present embodiment, the dummy 52 and the probe 56 are engaged by the adhesive agent 70 which is a resin material, and thus, the stress by the probe 56 is not easily transferred to microactuators 21 and 22 as compared to the engagement by chucking. Therefore, the flexure 10 can accurately be evaluated without causing damage to the contact surfaces 36a and 37a of the first fitting pads 36 and 37.

Furthermore, in the present embodiment, the slider 20 which is manufactured as a component of the hard disk drive 1 is used as the dummy 52. The slider 20 which is excellent in the solidity and processibility can achieve highly reproductive bonding strength tests. Moreover, since there is no necessity of designing and producing a new jig, the initial costs for the evaluation of the flexure 10 can be suppressed.

Furthermore, in the flexure 10 of FIG. 4, the tongue 33 of the metal base 30 is independent from the outrigger 32. In the evaluation of the above-structure flexure 10, if microactuators 21 and 22, tongue 33, and dummy 52 are engaged, possible strain and misalignment therebetween are suppressed, that is, undesirable factors in the bonding strength test can be reduced. In the present embodiment, not only the microactuators 21 and 22 but also the tongue 33 of the metal base 30 can be adhered to the dummy 52 by adjusting the injection of the adhesive agent 70. Therefore, the bonding strength between microactuators 21 and 22 and the first fitting pads 36 and 37 can be measured more stably by engaging microactuators 21 and 22, tongue 33, and dummy 52 together.

Now, first to third variations applicable to the bonding strength test method as explained with reference to FIGS. 9A to 10D will be explained. Each of the first to third variations is a bonding strength test method in which the bonding strength test device 50 of the present embodiment is used. The bonding strength test methods using the bonding strength test device 50 of the present embodiment can achieve the above-described advantages.

The first variation is explained with reference to FIGS. 11A to 11D. FIGS. 11A to 11D show the gimbal 13 of the flexure 10 as being viewed from the trailing side. The first variation differs from the bonding strength test method explained above with reference to FIGS. 9A to 10D in that only one of the microactuator 21 and 22 is fixed to the dummy 52 in the steps of FIGS. 9C and 9D (cf. FIGS. 11A and 11B).

Figure 12A:
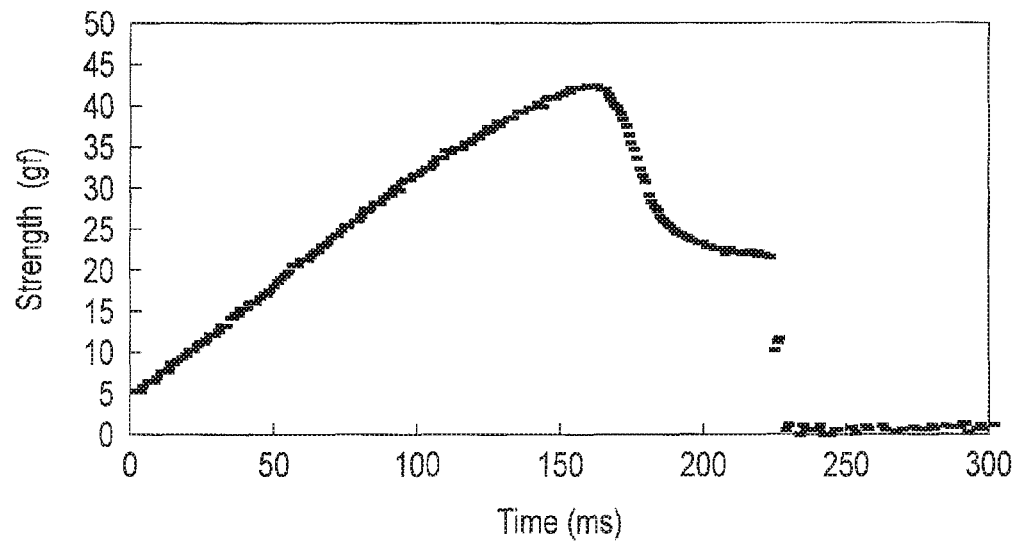
FIG. 12A is a graph which shows a result of the bonding strength test method shown in FIGS. 9A to 10D.
Figure 12B:
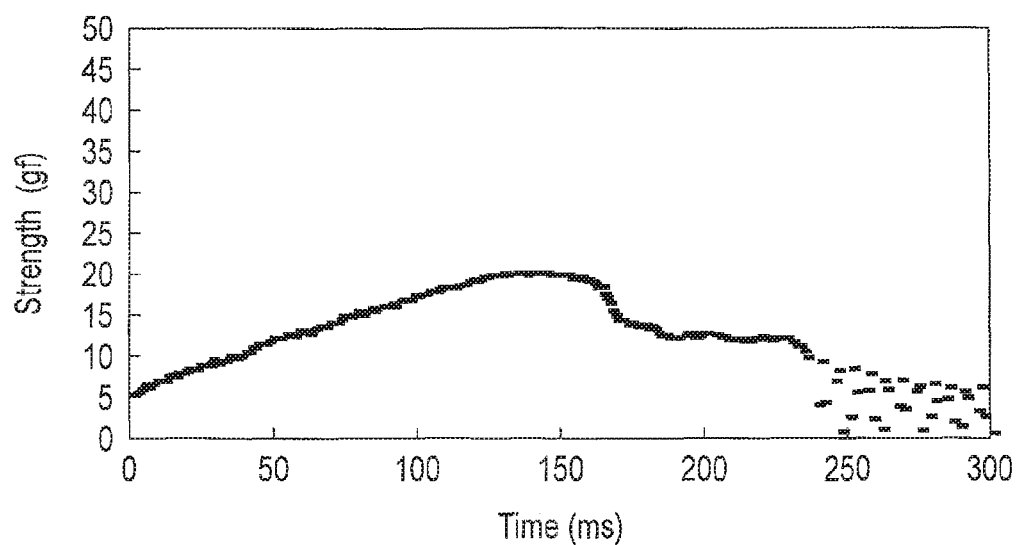
FIG. 12B is a graph which shows a result of the first variation of the method shown in FIGS. 11A to 11D.

FIG. 12A shows a result of the bonding strength test method explained with reference to FIGS. 9A to 10D. FIG. 12B shows a result of the first variation of the method explained with reference to FIGS. 11A to 11D.

FIG. 12A shows a peak which is a bonding strength measured at the time when one of the first ends 21a and 22a of the microactuators 21 and 22 is peeled off the flexure 10. The gradually reducing curve after the peak shows a bonding strength measured when the other end is peeled off the flexure 10.

FIG. 12B shows a peak which is a bonding strength measured at the time when the first end 21a of microactuator 21 is peeled off the flexure 10. The peak of two microactuators 21 and 22 of FIG. 12A is double as the peak of one microactuator 21 of FIG. 12B.

That is, in the bonding strength test method explained with reference to FIGS. 9A to 10D, the bonding strength of a pair of microactuators 21 and 22 can be measured at once while reducing the measurement time. Thus, the bonding strength can be evaluated efficiently. In the bonding strength test method explained with reference to FIGS. 11A to 11D, the bonding strength of one microactuator 21 can be evaluated.

Now, the second variation is explained in the second variation, the dummy 52 is pulled to be distant from the flexure 10 after the step of FIG. 10D. In this respect, the second variation differs from the bonding strength test method explained above with reference to FIGS. 9A to 10D. Note that, in the second variation, the tongue 33 of the metal base 30 is not adhered to the dummy 52 in the step of FIG. 9C.

The tongue 33 of the metal base 30 is continued to the outrigger 32 of the metal base 30 through the interconnection 40. Thus, when the dummy 52 is continuously pulled in a direction to be apart from the flexure 10, the second ends 21b and 22b of microactuators 21 and 22 are peeled off one after another the second fitting pads 38 and 39 on the tongue 33. In the second variation, the bonding strength of the second ends 21b and 22b of microactuators 21 and 22 can be measured in addition to the bonding strength of the first ends 21a and 22a.

Now, the third variation is explained. In the third variation, the tongue 30 of the metal base 30 is adhered and fixed to the base member 54a of the clamp 54 in the step of FIG. 10B. In this respect, the third variation differs from the bonding strength test method explained above with reference to FIGS. 9A to 10D. Note that, in the third variation, the tongue 33 of the metal base 30 is not adhered to the dummy 52 in the step of FIG. 9C.

When the dummy 52 is pulled in a direction to be apart from the flexure 10, the first and second ends 21a, 21b, 22a, and 22b of microactuators 21 and 22 are peeled off one after another the first and second fitting pads 36, 37, 38, and 39. In the third variation, the bonding strength of the first and second ends 21a, 21b, 22a, and 22b of microactuators 21 and 22 can be measured.

Now, an example of a bonding strength test device of a second embodiment will be explained with reference to FIG. 13. Structures the same as or similar to those of the first embodiment will be referred to by the same descriptions and reference numbers as in the first embodiment, and descriptions considered redundant will be omitted. The same structures and steps as in the first embodiment will be adopted in the second embodiment except for the following points.

In the bonding strength test device of the second embodiment, a dummy 52 is adhered to upper surfaces 21e and 22e of microactuators 21 and 22. In this respect, the second embodiment differs from the first embodiment. As a result, a tensile load in the loading and unloading directions is applied to the upper surfaces 21e and 22e of microactuators 21 and 22 instead of inner side surfaces 21f and 22f of microactuators 21 and 22.

The dummy 52 of the second embodiment may be formed larger than a slider 20 (which is shown in FIG. 3). Such a dummy 52 may be a slider mounted on a head gimbal assembly of old generations. The dummy 52 of the second embodiment has an outer shape similar to that of the dummy 52 of the first embodiment. That is, the dummy 52 of the second embodiment includes floating surfaces 52a and 52b, fixing surfaces 52b, side surfaces 52c, 52d, 52e, and 52f, and inclined surface 52g.

In the second embodiment, the dummy 52 is provided on the upper surfaces 21e and 22e of microactuators 21 and 22. The upper surfaces 21e and 22e of microactuators 21 and 22 are adhered to the fixing surface 52b of the dummy 52 by, for example, an ultraviolet-cured adhesive agent 70. Note that, in the example of FIG. 13, the side surfaces 52e and 52f are arranged parallel with microactuators 21 and 22; however, the side surfaces 52e and 52f may be arranged orthogonal to microactuators 21 and 22 by rotating the dummy 52.

The bonding strength test device 50 of the second embodiment can accurately measure a bonding strength (tensile strength) in the loading and unloading directions of a magnetic head. Therefore, the bonding strength between microactuators 21 and 22 and the flexure 10 can be evaluated accurately. As a result, the bonding strength of the flexure 10 of microactuators 21 and 22 is qualified.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

For example, an adhesive agent used for adherence of the microactuators and the dummy and adherence of the dummy and the probe may be other adhesive agents such as a cyanoacrylate adhesive agent. The lower end of the probe and the dummy can be engaged by chucking by providing a chuck on the upper surface of the dummy. A member used as a dummy is not limited to a slider. That is, to measure a bonding strength of an electronic component in a head gimbal assembly of a hard disk drive, various elements can be selected optionally as along as such an element is a solid material mounted to be adjacent to the electronic component but is not used in the head gimbal assembly.

What is claimed is:

1. A bonding strength test device configured to measure a bonding strength between a flexure of a suspension of a hard disk drive and electronic components mounted on a gimbal of the flexure, the bonding strength test device comprising:
   a clamp which fixes the flexure;
   a dummy adhered to the electronic components;
   a probe which engage with the dummy; and
   a device body which measures a tensile load applied to the probe while the probe is being pulled toward a direction to be apart from the flexure.

2. The bonding strength test device of claim 1, further comprising an adhesive agent for the engagement of the dummy and the probe.

3. The bonding strength test device of claim 1, wherein the electronic components are microactuators including a piezoelectric device formed of lead zirconate titanate, the gimbal includes a first surface on which a pair of microactuators are arranged to be separated from each other and a second surface opposite to the first surface, and the dummy includes side surfaces interposed between the microactuators to be adhered to inner side surfaces of the microactuators.

4. The bonding strength test device of claim 3, wherein the dummy is a slider mounted on the gimbal.

5. The bonding strength test device of claim 1, wherein the electronic components are microactuators including a piezoelectric device formed of lead zirconate titanate, the gimbal includes a first surface on which a pair of microactuators are arranged to be separated from each other and a second surface opposite, to the first surface, and the dummy is disposed on both upper surfaces of the pair of microactuators to be adhered to both the upper surfaces.

6. The bonding strength test device of claim 5, wherein the dummy is a slider having an outer dimension which is larger than that of a slider mounted on the flexure.

7. A method for measuring bonding strength between a flexure of a suspension of a hard disk drive and electronic components mounted on a gimbal of the flexure wherein the electronic components are microactuators including a piezoelectric device formed of lead zirconate titanate, the method comprising:

fixing the flexure to a clamp;
adhering a dummy to the microactuators;
engaging a probe in the dummy; and
measuring a tensile load between the probe and the flexure while pulling the probe in a direction to be apart from the flexure.

\* \* \* \* \*